United States Patent
Takano et al.

(10) Patent No.: US 7,605,146 B2
(45) Date of Patent: Oct. 20, 2009

(54) PROCESS FOR PRODUCING AN AMIDE COMPOUND

(75) Inventors: Naoyuki Takano, Ibaraki (JP); Daisaku Nakamura, Ichihara (JP)

(73) Assignee: Nihon Medi-Physics Company, Limited, Tokyo (JP)

( * ) Notice: Subject to any disclaimer, the term of this patent is extended or adjusted under 35 U.S.C. 154(b) by 1240 days.

(21) Appl. No.: 09/971,929

(22) Filed: Oct. 9, 2001

(65) Prior Publication Data

US 2002/0077456 A1 Jun. 20, 2002

(30) Foreign Application Priority Data

Oct. 11, 2000 (JP) .............................. 2000-310626

(51) Int. Cl.
*A01K 65/00* (2006.01)
*A61K 51/00* (2006.01)
*G01N 33/544* (2006.01)

(52) U.S. Cl. .............................. 514/69; 514/55; 514/62; 424/1.73; 436/529

(58) Field of Classification Search ........................ None
See application file for complete search history.

(56) References Cited

U.S. PATENT DOCUMENTS

| | | | |
|---|---|---|---|
| 5,021,571 A | * | 6/1991 | Mease et al. ................ 544/166 |
| 5,155,215 A | | 10/1992 | Ranney |
| 5,312,617 A | | 5/1994 | Unger et al. |
| 5,352,431 A | | 10/1994 | Hashiguchi et al. |
| 5,863,518 A | | 1/1999 | Hashiguchi et al. |
| 6,190,923 B1 | | 2/2001 | Johnson |

OTHER PUBLICATIONS

Hnatowich, et al., Int. J. Appl. Radiat. Isot., 1982, 33, 327-327.*
"Retrived from" website http://www.prospec.co.il/~prospec/cart/catalog/HSA.html#sequence [Oct. 20, 2006].*
Paik, et al., J. Nucl. Med. 1983, 1158-1163.*
[Retrieved from] http://www.800mainstreet.com/7/0007-008-le_chatelier.html, 2005, 5 pages [Retrieved on Aug. 1, 2007 ].*
Paik, et al., J. Nucl. Med. 1983, 1158-1163.*
Paik et al., The Journal of Nuclear Medicine, vol. 24, No. 12, pp. 1158-1163 (1983).
Hnatowich et al., Int. J. Appl. Radia. Isot., vol. 33, oo. 327-332 (1982).
Mortellaro et al., J. Am. Chem. Soc. 1996, 18, 7414-7415.

* cited by examiner

*Primary Examiner*—Andrew D Kosar
*Assistant Examiner*—Satyanarayana R Gudibande
(74) *Attorney, Agent, or Firm*—Birch, Stewart, Kolasch & Birch, LLP

(57) ABSTRACT

There is disclosed a process for producing an amide compound, which process is characterized in that a compound having an amino group are reacted with a polyaminopolycarboxylic acid anhydride in the presence of the polyaminopolycarboxylic acid.

17 Claims, No Drawings

SEQUENCE LISTING

```
<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: Synthetic Peptide
<221> NAME/KEY: MISC_FEATURE
<222> LOCATION: (1)..(1)
<223> OTHER INFORMATION: Xaa = Pyr

<400> SEQUENCE: 1

Xaa Lys Arg Pro Ser Gln Arg Ser Lys Tyr Leu
1               5                   10
```

PROCESS FOR PRODUCING AN AMIDE COMPOUND

BACKGROUND OF THE INVENTION

Field of the Invention

The present invention relates to a process for producing an amide compound having a polyaminopolycarboxylic acid group, which amide compound is a useful intermediate for pharmaceuticals, agricultural chemicals and the like. For example, an amide compound of formula (1) can be used as a diagnostic imaging agent by allowing the polyaminopolycarboxylic acid group to make a complex with a radioactive or paramagnetic metallic element.

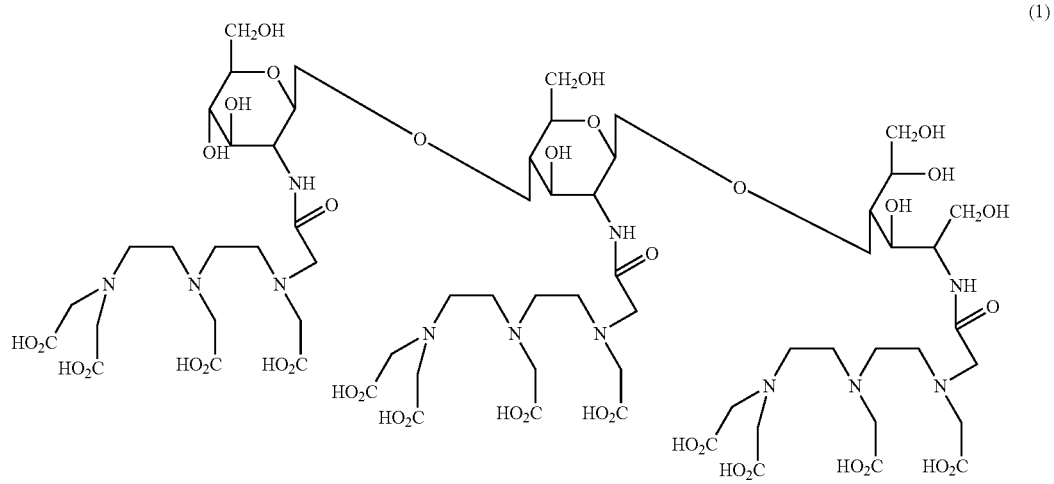

(1)

Heretofore, there has been known a process for producing an amide compound having a polyaminopolycarboxylic acid group, which process was conducted by mixing solid human serum albumin and solid polyaminopolycarboxylic acid anhydride, and quickly dissolving the mixture in a Hepes buffer solution (Int. J. Appl. Rad. Isot., 33, 327 (1982)). However, the process was not always satisfactory for practical industrial production in view of the operations of the process as described above.

SUMMARY OF THE INVENTION

According to the present invention, a desired amide compound can be readily and advantageously produced through practical industrial operations.

The present invention provides a process for producing an amide compound, which comprises reacting a compound having an amino group with a polyaminopolycarboxylic acid anhydride in the presence of the polyaminopolycarboxylic acid.

DETAILED DESCRIPTION OF THE INVENTION

The present invention will be described in detail below.

The compound having an amino group that may be used in the present invention is not particularly limited as long as it is an organic compound having at least one amino group in its molecule, and examples thereof include, for example, a protein, a peptide, an amino acid, an amino sugar, an amine and the like.

Examples of the protein include, for example, a blood protein such as serum albumin, fibrinogen or the like, a modified protein such as galactosyl serum albumin or the like, an enzyme such as amylase, pepsin or the like, an immune antibody such as IgG, or a fragment thereof such as Fab, Fab' or the like, a hormone such as thyroid-stimulating hormone, a growth hormone or the like, and a simple protein such as prolamine, glutelin or the like.

Examples of the peptide include, for example, a synthetic peptide such as Pyr-Lys-Arg-Pro-Ser-Gln-Arg-Ser-Lys-Tyr-Leu (SEQ ID NO:1), D-Phe-octreotide, polylysine or the like, a hormone such as oxytocin, bradykinin or the like, and an antibiotic such as valinomycin, colistin or the like.

Examples of the amino acid include, for example, an α-amino acid such as alanine, leucine, lysine or the like, a β-amino acid such as β-alanine, isoserine, or the like, a γ-amino acid such as γ-aminobutyric acid, 4-amino-3-hydroxybutyric acid or the like, and a δ-amino acid such as δ-aminovaleric acid, δ-aminolevulinic acid or the like.

Examples of the amino sugar include, for example, a monosaccharide such as glucosamine, galactosamine or the like, an amino oligosaccharide comprising glucosamine, galactosamine or the like as a repeating unit (e.g. chitosan oligosaccharide or the like), and a corresponding oligosaccharide having a reduced terminal reducing group.

Examples of the amino oligosaccharide include, for example, those having a molecular weight of 500 to 2000, and specific examples thereof include, for example, an oligosaccharide having 3 to 10 glucosamines or galactosamines as a repeating unit (e.g. chitosan tri- to decasaccharide comprising 3 to 10 D-glucosamines, or the like).

Examples of the amino oligosaccharides having a reduced terminal reducing group include, for example, glucosamine trisaccharide having a reduced terminal reducing group represented by the following formula (2):

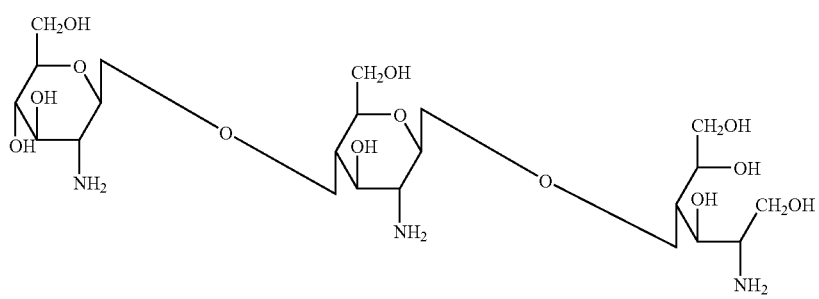

(2)

and a galactosamine trisaccharide having a reduced terminal reducing group represented by the following formula (3):

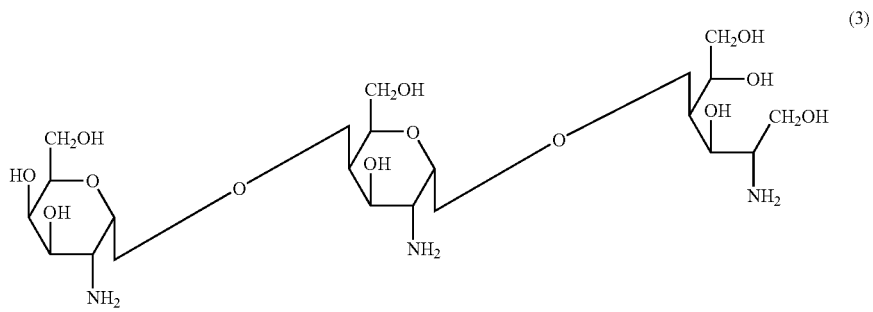

(3)

Examples of the amine include, for example, a monoamine such as aniline, 4-methylaniline, 4-octylaniline, ethylamine, n-propylamine, isopropylamine, n-butylamine, sec-butylamine, isobutylamine, tert-butylamine, n-octylamine, n-decylamine, (1-naphthylmethyl)amine, N-methylaniline, N-methyl-4-ethylaniline, N-methyl-4-octylaniline, diethylamine, N-ethyl-N-propylamine or the like, a diamine such as ethylenediamine, dansylethylenediamine, dansylhexamethylenediamine, N-(1-naphthyl)ethylenediamine, 1-naphthalenesulfonylethylenediamine, hexamethylenediamine, phenylenediamine or the like, and a triamine such as diethlenetriamine or the like.

The compound having an amino group may be used as it is or may also be used in the form of a solution or a suspension after being dissolved or suspended in a solvent described below. Furthermore, as a compound having an amino group, a salt comprising the compound having an amino group and a mineral acid such as hydrochloric acid, sulfuric acid or the like can also be used. When such a salt is used, it is desirable to mix the salt with an alkali in advance to convert the salt to a free amino group, or to add an alkali to the reaction system to convert the salt to a free amino group.

Examples of the polyaminopolycarboxylic acid anhydride include, for example, those having two or more amino groups and at least one acid anhydride group in the molecule such as ethylenediaminetetraacetic dianhydride, ethylenediaminetetraacetic acid monoanhydride, diethylenetriaminepentaacetic acid dianhydride, diethylenetriaminepentaacetic acid monoanhydride, 1,4,7,10-tetraazacyclododecane-1,4,7,10-tetraacetic dianhydride, 1,4,7,10-tetraazacyclodecane-1,4,7,10-tetraacetic acid monoanhydride or the like. The acid anhydride can be obtained by dehydrating corresponding polyaminopolycarboxylic acids by a conventional manner.

The polyaminopolycarboxylic acid monoanhydride may be obtained by adding water to polyaminopolycarboxylic acid dianhydride to hydrolyze one of its anhydride group.

The amount of the polyaminopolycarboxylic acid anhydride that may be used is not particularly limited and may suitably be set according to the desired amide compound, its application, its production cost or the like. For example, when a compound in which all the amino groups contained therein is amidated is desired, a polyaminopolycarboxylic acid anhydride is preferably used in an amount of one mole or more per mol of the amino groups in the compound having an amino group.

Examples of the polyaminopolycarboxylic acid include those having two or more amino groups and two or more carboxyl groups in the molecule such as ethylenediaminetetraacetic acid, diethylenetriamine-pentaacetic acid, 1,4,7,10-tetraazacyclodocecane-1,4,7,10-tetraacetic acid or the like. In this reaction, a polyaminopolycarboxylic acid corresponding to the polyaminopolycarboxylic acid anhydride is usually used. The polyaminopolycarboxylic acids as described above are commercially available.

The polyaminopolycarboxylic acid may be used as it is or may also be used after being converted to a carboxylate metal salt such as an alkali metal salt of the polyaminopolycarboxylic acid or an alkaline earth metal salt of the polyaminopolycarboxylic acid by mixing with an aqueous alkaline solution of, for example, an alkali metal hydroxide such as sodium hydroxide or the like, or an alkaline earth metal hydroxide such as magnesium hydroxide or the like.

The amount of the polyaminopolycarboxylic acid is usually 0.1 mole or more per mol of the polyaminopolycarboxylic acid anhydride. The amount has no particular upper limit, but in practical use, it is usually 5 moles, at most, per mol of the polyaminopolycarboxylic acid anhydride since too much use of the polyaminopolycarboxylic acid is economically disadvantageous.

The reaction temperature is usually 0° C. to the refluxing temperature of a reaction solution.

The present invention allows the compound having an amino group and the polyaminopolycarboxylic acid anhydride to react in the presence of the polyaminopolycarboxylic acid. For example, the process may be performed by adding the compound having an amino group and the polyaminopolycarboxylic acid anhydride to the polyaminopolycarboxylic acid, or by adding the acid anhydride to a mixture of the compound having an amino group and the polyaminopolycarboxylic acid. The compound having an amino group and the polyaminopolycarboxylic acid anhydride may be added to the polyaminopolycarboxylic acid simultaneously, for example, in such a way that their addition is finished at the same time or that the addition of one of them may be finished earlier than the other. In the latter case, it is preferred, particularly in an aqueous condition where water or a mixture of water and an organic solvent as described below is used as a solvent, to finish the addition of the compound having an amino group earlier than the addition of the polyaminopolycarboxylic acid anhydride from the viewpoint of the improvement in the yield of the desired compound. Alternatively, the compound having an amino group may be added to the polyaminopolycarboxylic acid, in the aqueous condition as described above, and subsequently the polyaminopolycarboxylic acid anhydride may be added. Under a non-aqueous condition where an organic solvent as described below is used as a solvent, the addition of the compound having an amino group and/or the polyaminopolycarboxylic acid is not limited to the methods as above, but the compound having an amino group may be added to a mixture of the polyaminopolycarboxylic acid anhydride and the polyaminopolyearboxylic acid. The compound having an amino group and/or the polyaminopolycarboxylic acid anhydride may be added either continuously or intermittently.

The reaction may be performed in the absence of a solvent, but is usually performed in the presence of a solvent because of the physical properties of the reaction mixture. Examples of the solvent include, for example, water, an organic solvent, or a mixture thereof.

Examples of the organic solvent include, for example, an alcohol solvent such as ethanol, 2-propanol, 1-butanol or diethylene glycol monomethyl ether, an aprotic polar solvent such as acetonitrile, N,N-dimethylformamide or dimethyl sulfoxide, an ether solvent such as diethyl ether, methyl tert-butyl ether, tetrahydrofuran and dioxane, a ketone solvent such as acetone, methyl ethyl ketone and methyl isobutyl ketone, an aromatic hydrocarbon solvent such as toluene, xylene, or the like, and a halogenated hydrocarbon solvent such as dichloromethane, dichloroethane, chloroform, carbon tetrachloride, chlorobenzene, dichlorobenzene or the like, and a mixture of the above-described solvents. Such organic solvents may be used alone or may also be used after being mixed.

The organic solvent may also be added to the compound having an amino group, the polyaminopolycarboxylic acid anhydride or the polyaminopolycarboxylic acid in advance. Water may be added to the compound having an amino group or the polyaminopolycarboxylic acid in advance, but it is desirable not to add water to the polyaminopolycarboxylic acid anhydride since there is a fear that mixing of water with the polyaminopolycarboxylic acid anhydride causes a hydrolysis reaction of the acid anhydride to proceed prior to the desired reaction.

The amount of the solvent that may be used is not particularly limited, but it is usually 100 parts by weight, at most, per 1 parts by weight of the compound having an amino group.

The reaction can proceed more smoothly by being performed in the presence of a base. Examples of the base include, for example, an inorganic base, an organic base and the like. Examples of the inorganic base includes, for example, an alkali metal hydroxide such as lithium hydroxide, sodium hydroxide, potassium hydroxide or the like, an alkaline earth metal hydroxide such as calcium hydroxide, magnesium hydroxide, or the like, an alkali metal carbonate such as lithium carbonate, sodium carbonate, potassium carbonate or the like, an alkali metal hydrogencarbonate such as sodium hydrogencarbonate, potassium hydrogencarbonate or the like.

Examples of the organic base include triethylamine, pyridine or the like. The amount of the base that may be used is not particularly limited, but it is, preferably, 50 moles, at most, per mol of the polyaminopolycarboxylic acid anhydride. Furthermore, such a base may be added to the compound having an amino group or the polyaminopolycarboxylic acid in advance.

When water is used as a solvent, it is desirable to perform the reaction while maintaining pH of the reaction solution in a weakly acidic to alkaline region from the viewpoint of the improvement in the yield of the desired compound. The pH range is preferably set in the range of pH 5 to 14, and more preferably in the range of pH 6 to 10. In this case, the reaction can be performed while the pH range of the reaction solution is adjusted within the aforesaid range through the addition of the aforementioned inorganic base to the reaction solution.

For example, when a polyaminopolycarboxylic acid anhydride having two or more anhydride groups in the molecule, such as ethylenediaminetetraacetic dianhydride, diethylenetriaminepentaacetic acid dianhydride or the like, is used to produce an amide compound having an amide group formed from one amino group and one anhydride group, and carboxyl groups resulted from hydrolysis of the rest of the anhydride group(s), the reaction can be performed while allowing sufficient amount of water for the hydrolysis to proceed in the reaction system or can be performed by using water as a reaction solvent. Particularly, using water as a reaction solvent is preferable since an amidation reaction and a ring-opening reaction can be performed simultaneously. When water is used as a reaction solvent, the pH of the reaction solution is usually adjusted during the reaction within a weakly acidic or alkaline region. The pH range is preferably set, for example, in a range of pH 5 to 14, and more preferably in a range of pH6 to 10.

After completion of the reaction, the desired amide compound can be isolated, through a refining treatment, if necessary.

When the reaction is performed in the presence of a base, there may be obtained an amide compound of which carboxylic acid group is forming a salt with the base.

When the compound having an amino group has a further hydroxyl group in the molecule, a polyaminopolycarboxylic acid anhydride may react with the hydroxyl group to form an esterified product. When such an esterified product is formed, it is preferable to adjust, after completion of the reaction, the reaction solution to weakly alkaline, for example, pH 8 to 10 to hydrolyze the esterified product, and thereafter the desired compound may be isolated.

Examples of the amide compound obtainable in such a way include, for example, a conjugate of a human serum albumin and diethylenetriaminepentaacetic acid, a conjugate of galactosyl serum albumin and diethylenetriamine-pentaacetic acid, a conjugate of D-Phe-octreotide and diethylenetriaminepentaacetic acid, an amide compound of formula (1),
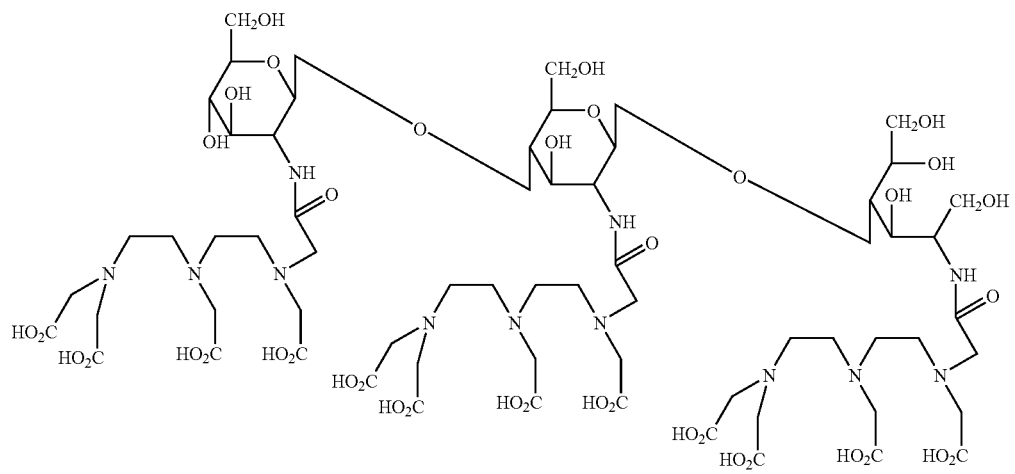
an amide compound of formula (4),
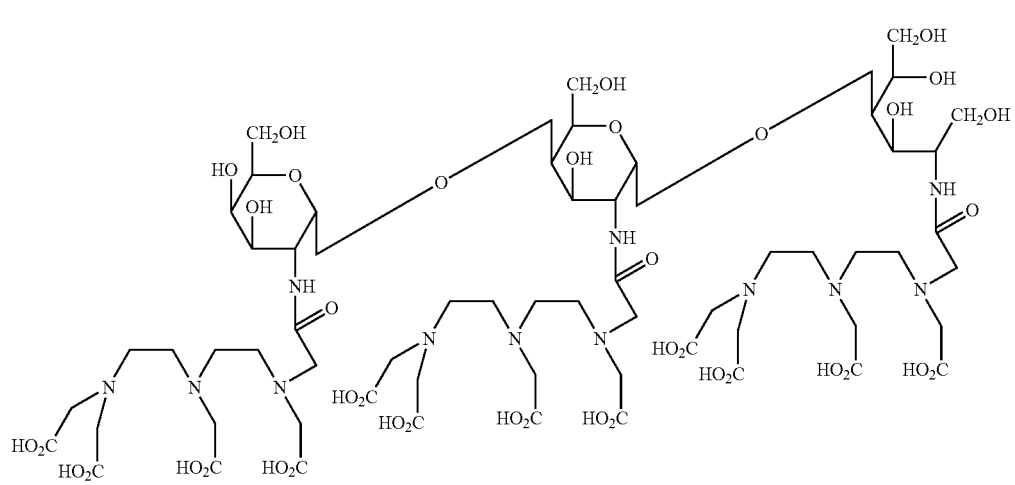
an amide compound of formula (5),
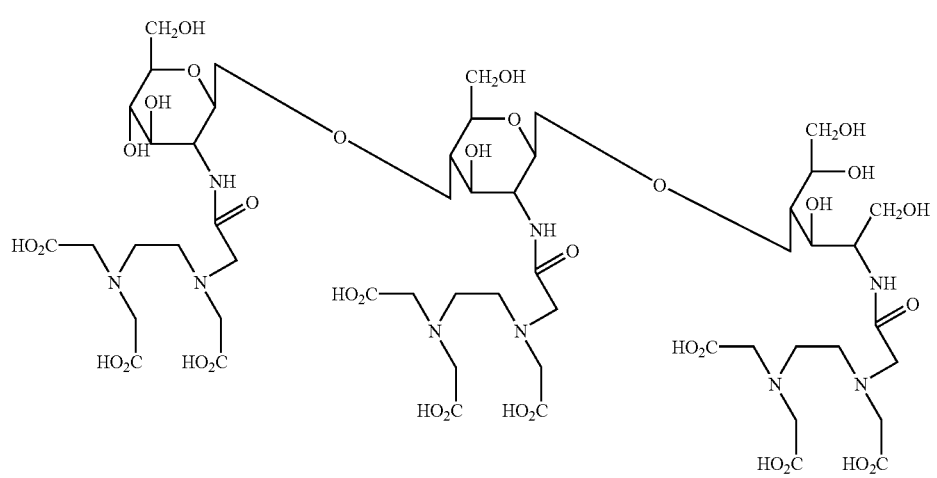

an amide compound of formula (6),
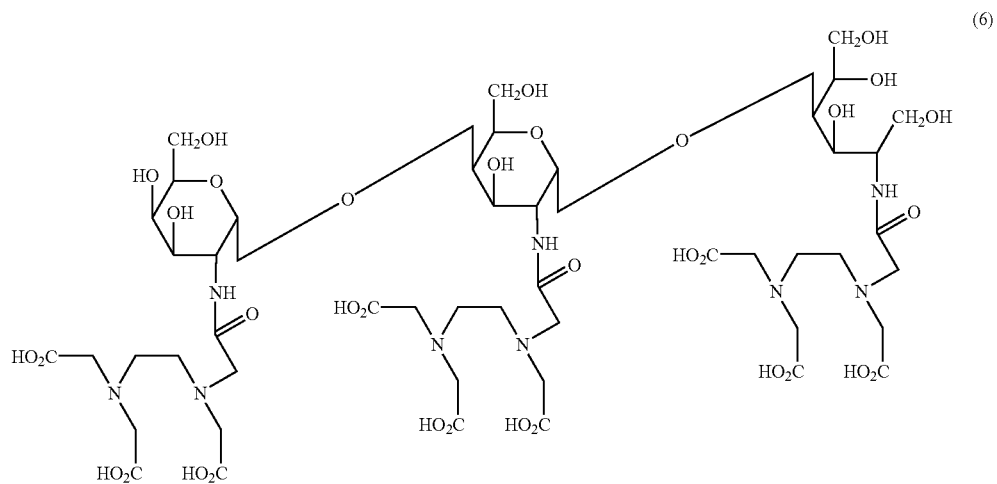
an amide compound of formula (7),
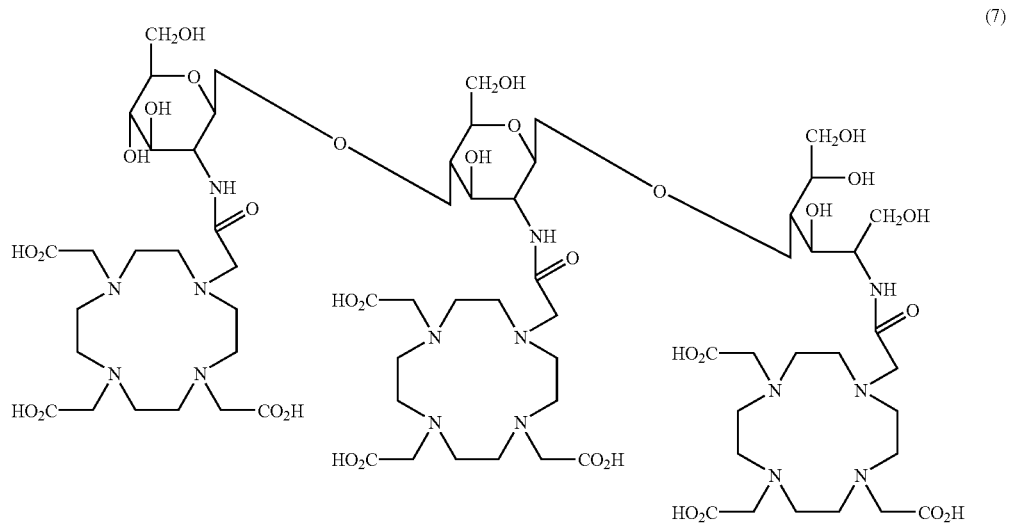
an amide compound of formula (8),
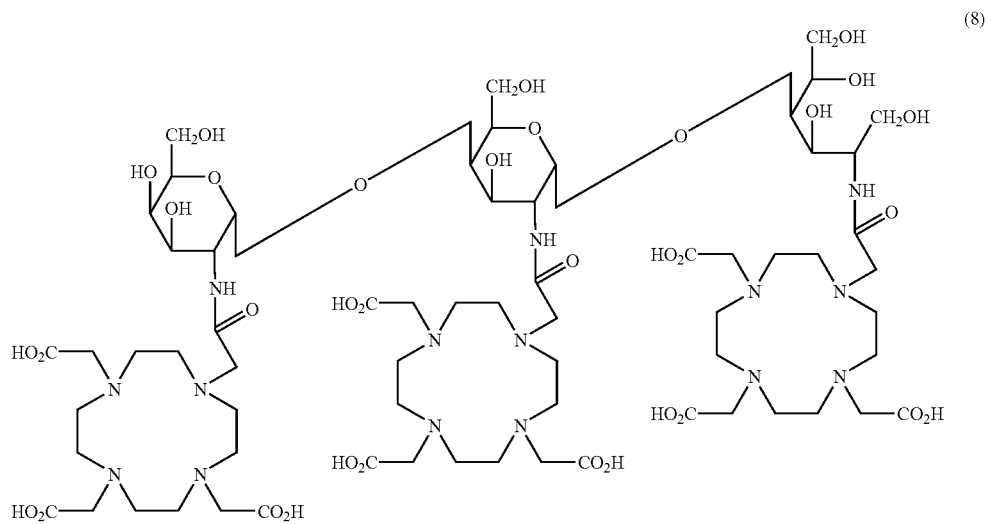

N-(phenylcarbamoylmethyl)diethylenetriamine-N,N',N",
N"-tetraacetic acid
N-(4-octylphenylcarbamoylmethyl)ethylenediamine-N,N',
N'-triacetic acid,
N-(4-octylphenylcarbamoylmethyl)diethylenetriamine-N,
N',N",N"-tetraacetic acid,
N-[(6-dansylaminohexyl)carbamoylmethyl]diethylenetri-
amine-N,N',N",N"-tetraacetic acid and
N,N"-bis(phenylcarbamoylmethyl)diethylenetriamine-N,N',
N"-triacetic acid.

Such a amide compound can be derivatized to a diagnostic imaging agent through, for example, coordination with a radioactive or paramagnetic metal element, and a refining treatment, if necessary.

EXAMPLES

Referring to examples, the present invention will be described in more detail below, but the present invention is not limited to these examples.

Example 1

Into a 500-mL five-necked separable flask equipped with a refluxing device, a stirring device and a thermometer was charged 131 g of a 16 wt % aqueous sodium hydroxide solution, and the internal temperature was raised to 80° C. After the addition of 3 g of a hydrochloric acid salt of chitosan trisaccharide having a reduced terminal producing group (chitotriitol) and 28.6 g of diethylenetriaminepentaacetic acid, 27.5 g of diethylenetriaminepentaacetic acid dianhydride was added continuously in small portions at the same temperature. After stirring and holding at the temperature for one hour, 31 g of a 30 wt % aqueous sodium hydroxide solution was added to adjust pH of the reaction solution to 9. After being stirred and maintained at the temperature for one hour, the mixture was cooled to room temperature. Analysis by high performance liquid chromatography revealed that the yield of the desired amide compound represented by the following formula (1) was 57.6%.

Example 2

Into a 500-mL five-necked separable flask equipped with a refluxing device, a stirring device and a thermometer were charged at room temperature 50 g of a 17 wt % aqueous sodium hydroxide solution and 28.8 g of diethylenetriaminepentaacetic acid, and the internal temperature was raised to 80° C. After the addition of 10 g of a 25 wt % aqueous sodium hydroxide solution at the same temperature, a solution dissolving 3 g of a hydrochloric acid salt of chitosan trisaccharide having a reduced terminal reducing group (chitotriitol) in 66 g of a 14 wt % aqueous sodium hydroxide solution, and 27.4 g of diethylenetriaminepentaacetic acid dianhydride were added simultaneously in paralell. The solution of chitosan trisaccharide having a reduced terminal reducing group (chitotriitol) and the diethylenetriaminepentaacetic acid dianhydride were added continuously over 25 minutes and 30 minutes, respectively. During the addition, pH of the reaction solution was in the range of 6.9 to 7.5. After completion of the addition, the reaction solution was stirred and maintained at the same temperature for one hour and then 36 g of a 25 wt % aqueous sodium hydroxide solution was added to adjust pH of the reaction solution to 9. After being stirred and maintained at the temperature for one hour, the mixture was cooled to room temperature. High performance liquid chromatography analysis revealed that the yield of the desired amide compound represented by the formula (1) above was 80.2%.

Example 3

Into a 500-mL five-necked separable flask equipped with a refluxing device, a stirring device and a thermometer were charged at room temperature 78 g of a 20 wt % aqueous sodium hydroxide solution and 51.7 g of diethylenetriaminepentaacetic acid, and the internal temperature was raised to 80° C. After the addition of 19 g of a 25 wt % aqueous sodium hydroxide solution at the same temperature, a solution of 3 g of a hydrochloric acid salt of chitosan trisaccharide having a reduced terminal reducing group (chitotriitol) in 57 g of a 16 wt % aqueous sodium hydroxide solution, and 27.5 g of diethylenetriaminepentaacetic acid dianhydride were added simultaneously in paralell thereto. The solution of chitosan trisaccharide having a reduced terminal reducing group (chitotriitol) and the diethylenetriaminepentaacetic acid dianhydride were added continuously over 25 minutes and 30 minutes, respectively. During the addition, pH of the reaction solution was in the range of 7.0 to 7.5. After completion of the addition, the reaction solution was stirred and maintained at the same temperature for one hour and then 44 g of a 25 wt % aqueous sodium hydroxide solution was added to adjust pH of

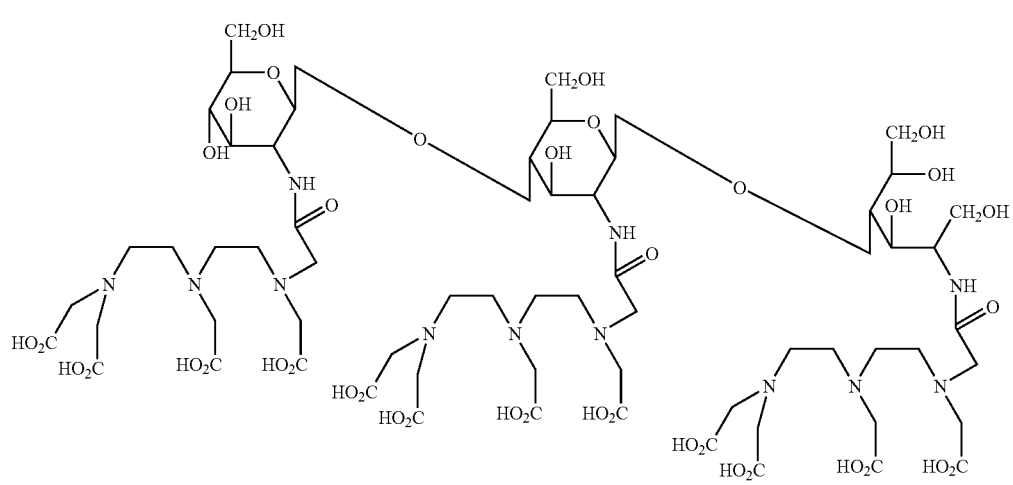

(1)

the reaction solution to 9. After being stirred and maintained at the temperature for one hour, the mixture was cooled to room temperature. High performance liquid chromatography analysis revealed that the yield of the desired amide compound represented by the formula (1) above was 82.1%.

Comparative Referential Example 1

Into a 500-mL five-necked separable flask equipped with a refluxing device, a stirring device and a thermometer were charged at room temperature 3 g of a hydrochloric acid salt of chitosan trisaccharide having a reduced terminal reducing group (chitotriitol) and 67 g of a 16 wt % aqueous sodium hydroxide solution, and the inner temperature was raised to 80° C. After the addition of 27.7 g of diethylenetriaminepentaacetic acid dianhydride in small portions at the same temperature, the reaction solution was stirred and maintained at the temperature for 15 minutes. After cooled to room temperature, high performance liquid chromatography analysis revealed that the yield of the desired amide compound of formula (1) above was 45.2%.

Example 4

Into a 500-mL five-necked separable flask equipped with a refluxing device, a stirring device and a thermometer were charged at room temperature 45 g of a 25 wt % aqueous sodium hydroxide solution, 40 g of 1,4-dioxane and 28.7 g of diethylenetriaminepentaacetic acid, and the internal temperature was raised to 73° C. At the same temperature, a solution of 3 g of a hydrochloric acid salt of a chitosan trisaccharide having a reduced terminal reducing group (chitotriitol) in 57 g of a 16 wt % aqueous sodium hydroxide solution, and 27.2 g of diethylenetriaminepentaacetic acid dianhydride were added simultaneously. The solution of chitosan trisaccharide having a reduced terminal reducing group (chitotriitol) and the diethylenetriaminepentaacetic acid dianhydride were added continuously in parallel over 25 minutes and 30 minutes, respectively. During the addition, pH of the reaction solution was in the range of 7.0 to 7.6. After completion of the addition, the reaction solution was stirred and maintained at the same temperature for 30 minutes and then 27 g of a 25 wt % aqueous sodium hydroxide solution was added to adjust pH of the reaction solution to 8. After being stirred and maintained at the same temperature for 30 minutes, the mixture was cooled to room temperature. High performance liquid chromatography analysis revealed that the yield of the desired amide compound represented by the formula (1) above was 67.2%.

Example 5

Into a 100-mL four-necked flask equipped with a refluxing device, a stirring device and a thermometer were charged at room temperature 1 g of a hydrochloric acid salt of chitosan trisaccharide having a reduced terminal reducing group (chitotriitol), 34 g of a 16 wt % aqueous sodium hydroxide solution and 7.2 g of ethylenediaminetetraacetic acid. After the internal temperature was raised to 80° C., 6.3 g of ethylenediaminetetraacetic dianhydride was added continuously in small portions. After being stirred and kept at the temperature for 30 minutes, 16 g of a 11 wt % aqueous sodium hydroxide solution was added to adjust pH of the reaction solution to 9. After being stirred and maintained at the temperature for 30 minutes, the mixture was cooled to room temperature. High performance liquid chromatography analysis revealed that the desired amide compound of formula (5) was obtained, wherein corrected area percentage of the compound in chromatogram was 51%. LC/ESI mass analysis: m/z=1326.9 ([M+H]$^+$), m/z=1324.9 ([M−H]$^+$).

$$(5)$$

Example 6

Into a 200-mL four-necked flask equipped with a refluxing device, a stirring device and a thermometer were charged at room temperature 80 mL of N,N-dimethylformamide (dehydrated) and 6.6 g of diethylenetriaminepentaacetic acid, and the internal temperature was raised to 75° C. After the addition of 6.0 g of diethylenetriamine-pentaacetic acid dianhydride at the temperature and subsequently being stirred and maintained for 30 minutes at the same temperature, 0.3 g of water was added in small portions in order to convert the dianhydride to a monoanhydride. After additional stirring and maintaining for one hour at the same temperature, 3.5 g of 4-octylaniline was added dropwise over 10 minutes. After being stirred and kept for one hour at the same temperature, the filtrate obtained by filtration to remove insoluble matters was concentrated to yield 11.8 g of crude crystals. High performance liquid chromatography analysis of the crude crystals confirmed that the desired N-(4-octylphenylcarbamoylmethyl)diethylenetriamine-N,N',N''-tetraacetic acid was obtained (the corrected area percentage in chromatogram: 94.3%).

The invention claimed is:

1. A process for producing an amide compound, which comprises reacting a compound having an amino group with a polyaminopolycarboxylic acid anhydride in the presence of the polyaminopolycarboxylic acid,
   wherein the polyaminopolycarboxylic acid anhydride is added to a mixture of the compound having an amino group and the polyaminopolycarboxylic acid, or the compound having an amino group and the polyaminopolycarboxylic acid anhydride are added to the polyaminopolycarboxylic acid,
   wherein the polyaminopolycarboxylic acid anhydride is ethylenediaminetetraacetic dianhydride, ethylenediaminetetraacetic acid monoanhydride, diethylenetriaminepentaacetic acid dianhydride, 1,4,7,10-tetraazacyclododecane-1,4,7,10-tetraacetic dianhydride, or 1,4,7,10-tetraazacyclododecane-1,4,7,10-tetraacetic acid monoanhydride; and
   wherein the polyaminopolycarboxylic group of both said acid and said acid anhydride are the same.

2. The process according to claim 1, wherein the compound having an amino group is a protein, a peptide, an amino acid, an amino sugar or an amine.

3. The process according to claim 2, wherein the amino sugar is an amino oligosaccharide or an amino oligosaccharide having a reduced terminal reducing group.

4. The process according to claim 3, wherein the molecular weight of the amino oligosaccharide is 500 to 2000.

5. The process according to claim 4, wherein the amino oligosaccharide having a molecular weight of 500 to 2000 is a glucosamine oligosaccharide or a galactosanino oligosaccharide.

6. The process according to claim 5, wherein the galactosamino oligosaccharide is a galactosamine tri- to decasaccharide.

7. The process according to claim 1, wherein the polyaminopolycarboxylic acid anhydride is added to a mixture of the compound having an amino group and the polyaminopolycarboxylic acid.

8. The process according to claim 1, wherein the compound having an amino group and the polyaminopolycarboxylic acid anhydride are added to the polyaminopolycarboxylic acid.

9. The process according to claim 8, wherein the compound having an amino group and the polyaminopolycarboxylic acid anhydride are added simultaneously to the polyaininopolycarboxylic acid.

10. The process according to claim 1, wherein the reaction is performed in the presence of a solvent.

11. The process according to claim 10, wherein the solvent is at least one selected from the group consisting of water and an organic solvent.

12. The process according to claim 11, wherein the solvent is water.

13. The process according to claim 1, wherein the compound having an amino group is a chitosan tri- to deca-saccharide, a chitosan tri- to deca-saccharide having a reduced terminal reducing group, a galactosamine tri- to deca-saccharide, a galactosamine tri- to deca-saccharide having a reduced terminal reducing group, serum albumin, fibrinogen, galactosyl serum albumin, amylase, pepsin, IgG, Fab, Fab', thyroid-stimulating hormone, a growth hormone, prolamine, glutelin, Pyr-Lys-Arg-Pro-Ser-Gln-Arg-Ser-Lys-Tyr-Leu (SEQ ID NO:1), D-Phe-octreotide, polylysine, oxytocin, bradykinin, valinomycin, colistin, an α-amino acid, a β-amino acid, a γ-amino acid, aniline, 4-methylaniline, 4-octylaniline, ethylamine, n-propylamine, isopropylamine, n-butylamine, sec-butylamine, isobutylamine, tert-butylamine, n-octylamine, n-decylamine, (1-naphthylmethyl)amine, N-methylaniline, N-methyl-4-ethylaniline, N-methyl-4-octylaniline, diethylamine, N-ethyl-N-propylamine, ethylene diamine, dansylethylenediamine, dansyihexamethylenediamine, N-(1-naphthyl)ethylenediamine, 1-naphthalenesulfonylethylenediamine, hexamethylenediamine, or phenylenediamine.

14. The process according to claim 1, wherein the amide compound is a conjugate of a human serum albumin and diethylenetriaminepentaacetic acid,
   a conjugate of galactosyl serum albumin and diethylenetriamine-pentaacetic acid,
   a conjugate of D-Phe-octreotide and diethylenetriamine-pentaacetic acid, an amide compound of formula (1),
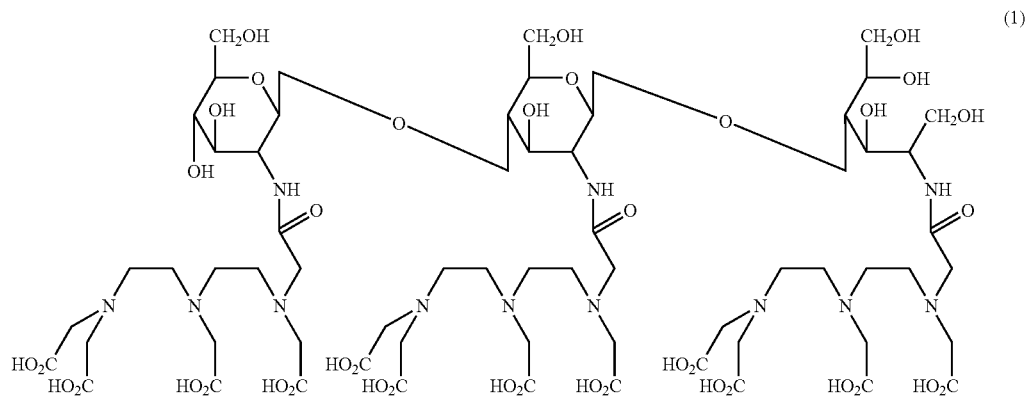
an amide compound of formula (4),
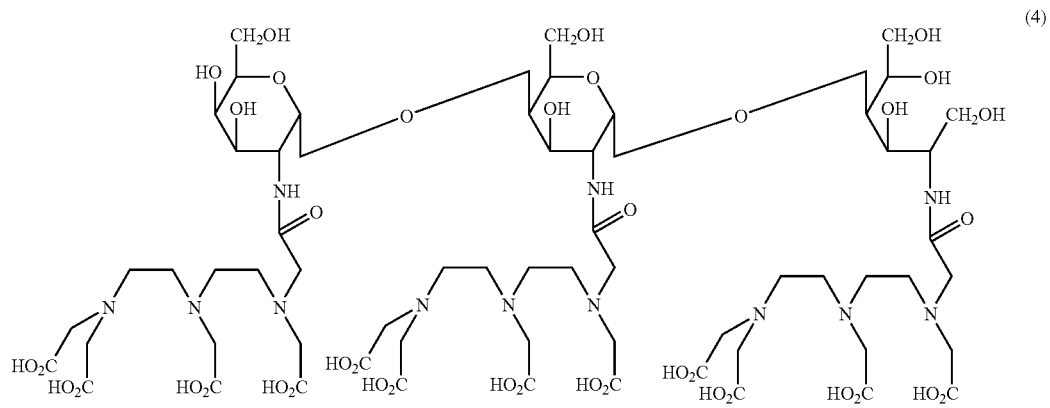
an amide compound of formula (5),
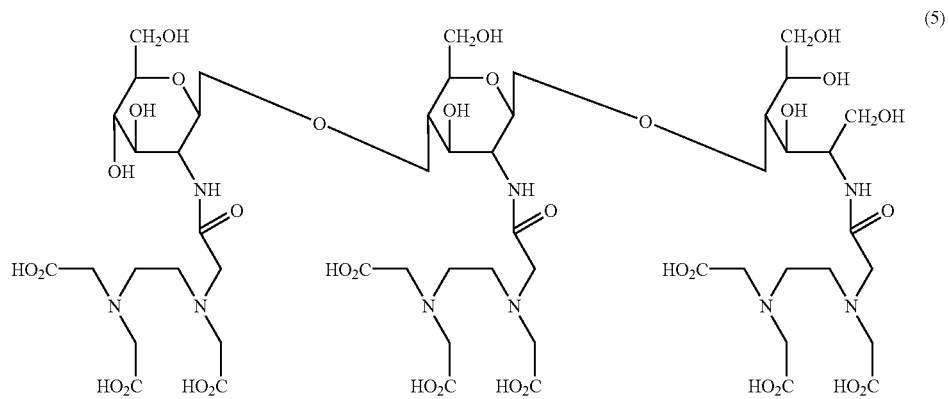

an amide compound of formula (6),
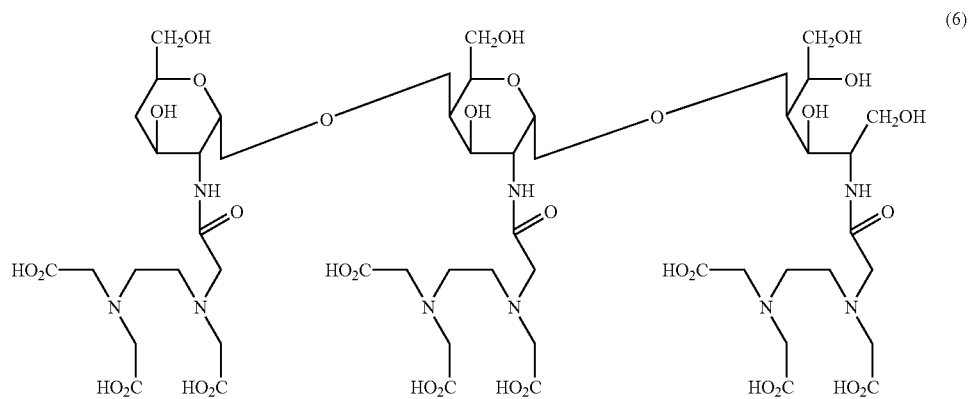
an amide compound of formula (7),
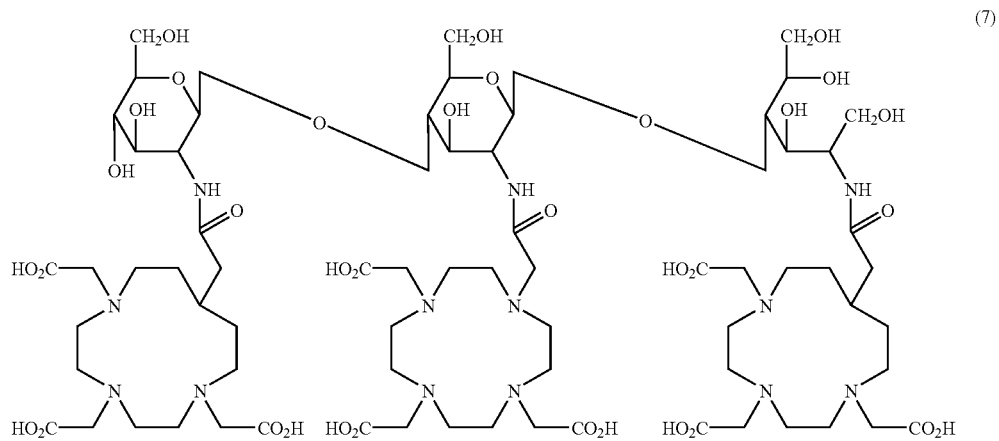
an ainide compound of formula (8),
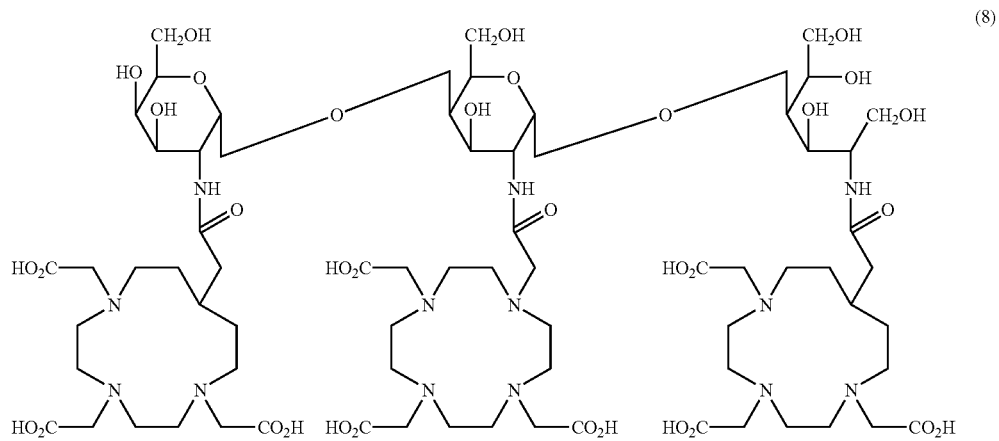

N-(phenylcarbamoylmethyl)diethylenetriamine-N,N',N",N"-tetraacetic acid, N-(4-octylphenylcarbamoylmethyl)ethylenediamine-N,N",N"-triacetic acid, N-(4-octylphenylcarbamoylmethyl)diethylenetriamine-N,N',N",N"-tetraacetic acid, N-[(6-dansylaminohexyl)carbamoylmethyl]diethylenetriamine-N,N',N",N"-tetraacetic acid, or N,N"-bis(phenylcarbamoylmethyl)diethylenetriamine-N,N',N"-triacetic acid.

15. A process for producing an amide compound, which comprises reacting a compound having an amino group with a polyaminopolycarboxylic acid anhydride in the presence of the polyaminopolycarboxylic acid; wherein the compound having an amino group is a chitosan tri- to deca-saccharide,
    wherein the polyaminopotycarboxylic acid anhydride is added to a mixture of the compound having an amino group and the polyaminopolycarboxylic acid, or the compound having an amino group and the polyaminopolycarboxylic acid anhydride are added to the polyaminopolycarboxylic acid,
    wherein the polyaminopolycarboxylic acid anhydride is ethylenediaminetetraacetic dianhydride, ethylenediaminetetraacetic acid monoanhydride, diethylenetriaminepentaacetic acid dianhydride, 1,4,7,10-tetraazacyclododecane-1,4,7,10-tetraacetic dianhydride, or 1,4,7,10-tetraazacyclododecane-1,4,7,10-tetraacetic acid monoanhydride; and
    wherein the polyaminopolycarboxylic group of both said acid and said acid anhydride are the same.

16. A process for producing an amide compound, which comprises reacting a compound having an amino group with a polyaminopolycarboxylic acid anhydride in the presence of the polyaminopoilycarboxylic acid; wherein the polyaminopolycarboxylic acid is ethylenediamine-tetraacetic acid, diethylenetriamine-pentaacetic acid, or 1,4,7,10-tetraazacyclododecane-1,4,7,10-tetraacetic acid,
    wherein the polyaminopdycarboxylic acid anhydride is added to a mixture of the compound having an amino group and the polyaminopolycarboxylic acid, or the compound having an amino group and the polyaminopolycarboxylic acid anhydride are added to the polyaminopolycarboxylic acid; and
    wherein the polyaminopolycarboxylic group of both said acid and said acid anhydride are the same.

17. A process for producing an amide compound, which comprises reacting a compound having an amino group with a polyaminopolycarboxylic acid anhydride in the presence of the polyaminopolycarboxylic acid and a base,
    wherein the polyaminopolycarboxylic acid anhydride is added to a mixture of the compound having an amino group and the polyaminopolycarboxylic acid, or the compound having an amino group and the polyaminopolycarboxylic acid anhydride are added to the polyaminopolycarboxylic acid,
    wherein the polyaminopolycarboxylic acid anhydride is ethylenediaminetetraacetic dianhydride, ethylenediaminetetraacetic acid monoanhydride, diethylenetriaminepentaacetic acid dianhydride, 1,4,7,10-tetraazacyclododecane-1,4,7,10-tetraacetic dianhydride, or 1,4,7,10-tetraazacyclododecane-1,4,7,10-tetraacetic acid monoanhydride; and
    wherein the polyaminopolycarboxylic group of both said acid and said acid anhydride are the same.

* * * * *